United States Patent [19]

Contractor et al.

[11] Patent Number: 5,895,821
[45] Date of Patent: Apr. 20, 1999

[54] PROCESS FOR THE CALCINATION/ ACTIVATION OF V/P/O CATALYST

[75] Inventors: Rashmikant Maganlal Contractor, Ardentown; Harold Saul Horowitz, Wilmington; Gregory Scott Patience, Wilmington; John Donal Sullivan, Wilmington, all of Del.

[73] Assignee: E. I. du Pont de Nemours and Company, Wilmington, Del.

[21] Appl. No.: 08/940,718

[22] Filed: Sep. 30, 1997

[51] Int. Cl.⁶ .................................................. C07D 307/60
[52] U.S. Cl. ........................................... 549/259; 502/209
[58] Field of Search ............................ 549/259; 502/209

[56] References Cited

U.S. PATENT DOCUMENTS

| | | | |
|---|---|---|---|
| 3,915,892 | 10/1975 | Harrison | 252/435 |
| 4,371,702 | 2/1983 | Bither, Jr. | 549/260 |
| 4,668,802 | 5/1987 | Contractor | 549/259 |
| 4,677,084 | 6/1987 | Bergna | 502/8 |
| 4,748,140 | 5/1988 | Blum et al. | 502/209 |
| 5,021,588 | 6/1991 | Contractor | 549/259 |
| 5,573,992 | 11/1996 | Contractor et al. | 502/209 |

*Primary Examiner*—Bernard Dentz

[57] ABSTRACT

An improved process for calcination and activation of a catalyst containing mixed oxides of vanadium and phosphorus (V/P/O) involving the addition of spray dried catalyst precursor to a fluidizing oxygen containing gas at a controlled rate such that the temperature is maintained at a range of 370 to 410° C. (preferably 390±5° C.). The catalyst precursor experiences, in addition to rapid temperature rise, dehydration/calcination at this elevated temperature in the fluidized state for an average range of residence time of less than about 4 hours at 3.5 atm of air or above, and up to 20 hours at 1 atm of air while simultaneously and continuously maintaining an average $V_{ox}$ of 4.55 or less. Such a process is useful in preparing a V/P/O catalyst that exhibits enhanced activity for the oxidation of n-butane to maleic anhydride. The novel process also provides an improved method for start-up of a commercial scale recirculating solids reactor.

8 Claims, No Drawings

PROCESS FOR THE CALCINATION/ACTIVATION OF V/P/O CATALYST

CROSS-REFERENCE TO RELATED APPLICATIONS

Not Applicable.

BACKGROUND OF THE INVENTION

1. Field of the Invention

This invention relates to an improved process for the calcination and activation of a catalyst containing mixed oxides of vanadium and phosphorus (V/P/O) useful in the preparation of maleic anhydride from n-butane. More specifically but not by way of limitation, the present invention relates to a method of calcination of a V/P/O catalyst by inducing a very rapid temperature rise while in an oxidizing fluidized state and a novel method of accomplishing this within a transfer bed commercial scale plant.

2. Description of the Related Art

The vapor phase oxidation of n-butane to maleic anhydride over a V/P/O catalyst is generally known in the art. A review of the prior art describing this process is given in U.S. Pat. No. 4,668,802. In improved processes described in U.S. Pat. No. 4,668,802 and U.S. Pat. No. 5,021,588 the reaction is conducted in a recirculating solids reactor having two fluidized reaction zones. The conversion of n-butane to maleic anhydride takes place primarily in one reaction zone and the catalyst, essentially stripped of gaseous species, is transported to the other reaction zone where it is re-oxidized; i.e., regenerated prior to being returned to the reaction zone.

The mixed oxide V/P/O compositions used as catalysts in these processes are known to the art. A review of the art describing V/P/O compositions and their preparation is given in U.S. Pat. No. 4,371,702. The catalyst precursor composition is usually made by a process wherein a conventional vanadium compound in which the vanadium is in the +5 oxidation state, such as in $V_2O_5$ or $NH_4VO_3$, is partially reduced to the +4 oxidation state by reaction in either an aqueous or organic liquid medium. The catalyst precursor is then formed by the addition of any appropriate phosphorus compound, for example $H_3PO_4$, refluxing to bring about reaction and recovering the catalyst precursor, usually as a hydrated vanadium phosphate, by filtration and drying or spray drying. The prior art describes the desirable range of atomic ratios of phosphorus to vanadium and also the incorporation of catalyst promoters. It is desirable that the V/P/O catalyst has good attrition resistance particularly when it is used in a fluidized bed or recirculating bed reactor. The prior art relevant to attrition resistant catalyst and its preparation is reviewed in U.S. Pat. No. 4,677,084. The production of V/P/O catalysts useful for the preparation of maleic anhydride from n-butane requires controlled calcination and activation of the catalyst precursor. This is accomplished by heating the precursor under appropriate temperature, time and atmosphere conditions to accomplish dehydration, while maintaining the average vanadium oxidation state (Vox) between specified limits. For example in U.S. Pat. No. 3,915,892 the precursor dihydrate is converted to the monohydrate by evolving one water of hydration at 370° C. to 394° C. while maintaining the Vox in the range of 4.1 to 4.5. The balance of the water is then removed by heating at 395° C. to 425° C. followed by promoting a bulk crystal phase transition above 450° C. in a carrier gas consisting of air or an inert gas together with controlled amounts of oxygen and hydrocarbon to provide an effluent stream containing at least one volume percent of oxygen or one volume percent each of oxygen and hydrocarbon, again while maintaining the Vox in the range of 4.1 to 4.5.

When the calcination/activation procedures described in the prior art are used to prepare V/P/O catalyst on the scale necessary to provide catalyst for commercial operation it is found that, from the standpoint of maleic anhydride production from n-butane, the resulting catalyst is inferior, to catalyst made on a small batch basis. Consequently more stringently controlled process conditions are needed to produce high grade catalyst on a scale required for commercial plant operation. For example, in U.S. Pat. No. 5,573,992 issued Nov. 12, 1996, a relatively low pressure process for calcination and activation of a catalyst containing mixed oxides of vanadium and phosphorus within limited specified operating conditions is disclosed. This process involved the steps of calcining a hydrated V/P/O or V/P/O-$SiO_2$ catalyst precursor at a temperature range of 375° C. to 400° C. for sufficient time to dehydrate the catalyst precursor while simultaneously and continuously controlling the oxygen level such as to maintain the Vox in the range of 3.825 to 4.175; and then activating the dehydrated catalyst precursor by further heating at a range of 340° C. to 500° C. in the presence of a gaseous atmosphere containing n-butane at a partial pressure not exceeding 0.20 atm while simultaneously and continuously controlling the oxygen level such as to maintain the Vox in the range of 3.95 to 4.15. The instant invention is viewed as an improvement over this process.

BRIEF SUMMARY OF THE INVENTION

The present invention relates to an improved process for calcining and activating a V/P/O catalyst precursor at elevated temperature and pressure during the preparation of a highly active and selective V/P/O catalyst capable of producing a high yield of maleic anhydride by the oxidation of n-butane. For purposes of this invention the catalyst activity is to be defined with respect to n-butane oxidation, the selectivity relates to maleic anhydride production and yield is a function of activity and selectivity. The present invention further relates to a method of starting up a commercial scale fluidized transfer bed plant that takes advantage of the improved elevated temperature and pressure calcination and activation of V/P/O catalyst precursor in situ. The process of this invention is particularly suited to the large scale production of catalyst for use in recirculating bed reactors associated with the commercial scale production of maleic anhydride typically resulting in substantial reduction in start-up time while simultaneously producing catalyst of significantly higher activity.

Thus the present invention provides a process for calcining V/P/O catalyst comprising the steps of:

(a) establishing a gas flow within a fluidized bed reactor using air or oxygen containing gas at a temperature range of 370° C. to 420° C.;

(b) adding to the fluidized bed reactor of step (a) a hydrated V/P/O or V/P/O-$SiO_2$ catalyst precursor at a rate such that the catalyst precursor experiences a rapid temperature rise in a fluidized bed state to a temperature range of 370° C. to 420° C.;

(c) maintaining the catalyst precursor of step (b) in a fluidized state at the temperature range for a sufficient time and pressure to remove entrained organics and to dehydrate the catalyst precursor while simultaneously achieving an average Vox in excess of 4.05 but not in excess of 4.55; and (d) recovering and storing the calcined V/P/O catalyst produced in step (c) in a non-oxidizing gas.

The improved method of starting up a commercial scale transfer bed plan t involves in a process for selective vapor phase oxidation of n-butane to maleic anhydride involving the use of a recirculating solids reactor comprising a reaction zone and a catalyst regeneration zone wherein n-butane is converted to maleic anhydride in the reaction zone of the recirculating solids reactor by use of a vanadium/phosphorous oxide (V/P/O) catalyst in oxidized form and the reduced vanadium/phosphorous oxide catalyst is regenerated by contact with oxygen in the regeneration zone of the recirculating solids reactor; the specific improvement comprising: (i) adding catalyst precursor to the regeneration zone maintained at a temperature between 380° C. and 400° C.; (ii) maintaining the catalyst precursor in a fluidized state within the regeneration zone by use of air or oxygen containing gas for a sufficient time and pressure to remove entrained organics and to dehydrate the catalyst precursor; (iii) transferring calcined catalyst precursor from the regeneration zone to the reaction zone such as to maintain an average residence time for catalyst precursor in the regeneration zone resulting in an average $V_{ox}$ of 4.55 or less; and (iv) maintaining the calcined catalyst precursor in a fluidized state within the reaction zone near operating temperature using a substantially non-oxidizing gas until catalyst circulation is commenced.

In one embodiment of the commercial scale start-up according to the present invention, the rate of addition of catalyst precursor is coordinated simultaneously with the transferring of calcined catalyst precursor from the regeneration zone to the reaction zone such as to maintain the temperature within the regeneration zone until the entire charge of catalyst is calcined. In a related embodiment the charge of calcined catalyst precursor is activated, in situ, under operating conditions with introduction of n-butane to the reaction zone and catalyst recirculation between the reaction zone and the regeneration zone. Preferably the catalyst precursor is maintained at a temperature of 390±5° C. In the commercial start-up embodiments the catalyst precursor is maintained in a fluidized state within the regeneration zone at a pressure up to about 3.5 atm and the average residence time for catalyst precursor in the regeneration zone is maintained at less than about 4 hours at 3.5 atm of air or above and up to 20 hours at 1 atm of air. Optionally, the temperature range of 380° C. to 400° C. is achieved by direct fire heating using n-butane resulting in a water vapor content in the air or oxygen containing gas of up to about 3 mole %.

It is an object of the present invention to provide a simplified and quick method of calcining and activating particulate V/P/O catalyst precursor on a commercial scale. It is an associated object to significantly reduce the time required to start-up a contemporary transfer fluidized bed commercial scale plant using such V/P/O catalyst. It is a further object of the present invention to provide a method of calcining a V/P/O catalyst precursor that results in a catalyst of enhanced activity and surface area but not at the expense of selectivity.

DETAILED DESCRIPTION OF THE INVENTION

This invention relates to a process for the preparation of a highly active and selective V/P/O catalyst capable of producing a high yield of maleic anhydride by the oxidation of n-butane. The vanadium pyrophosphate catalyst required for this reaction needs to be transformed from precursor to active crystalline phase by a calcination/activation procedure. Also, the elevated temperature and pressure calcination/activation process of this invention can be used for preparing V/P/O catalyst on any scale but it is particularly suited to the start-up of large scale production facility employing a recirculating solids reactor. Prior to the improved method associated with the instant invention, the start-up procedure for a commercial recirculating solids reactor intended to selectively oxidize n-butane to maleic anhydride included calcination/activation of the precursor envisioned as a batch process which would require several weeks to complete. The improved method according to the present invention conceptually is an in situ start-up process where the calcination/activation procedure can be accomplished in several days. Preferably the desired calcination is carried out continuously or semi-continuously in the catalyst regenerator vessel of the commercial plant in about the time required to load and heat the catalyst to 390° C. in air at 2.5 to about 3.5 atm. During this time the riser vessel of the recirculating solids reactor is maintained at approximately the same temperature in substantially an inert atmosphere. The calcined catalyst produced in the regeneration zone is periodically or continuously transferred to the reactor vessel (i.e., to the riser side of the plant) such as to maintain an average residence time in the regenerator of less than a critical maximum duration which is a function of operating pressure and temperature of the regenerator (e.g., typically 4 hours maximum residence time at about 3.5 atm up to 20 hours maximum residence time at about 1 atm of air at about 390° C.).

In order to more fully appreciate and understand the justification, benefits and advantages of this operating procedure for calcination/activation of V/P/O catalyst in a commercial scale recirculating solids reactor, it is perhaps best to consider not only certain experimental data related to catalyst variables such as temperature, time, pressure including partial pressure of oxygen and water, combustion of residual organics in the catalyst precursor and average vanadium oxidation state (i.e., $V_{ox}$), but also certain pragmatic plant design and engineering constraints typical of a commercial scale operation.

Temperature

According to the improved method for calcining catalyst precursor of the instant invention, spray dried V/P/O catalyst precursor or the like is initially introduced either into a hot fluidized bed reactor or into a hot fluidized bed of calcining precursor within a fluidized bed reactor while the fluidizing gas, fluid bed reactor and/or fluidized bed are maintained at operating temperature. In other words, the V/P/O catalyst precursor to be calcined is initially introduced into the fluid bed reactor under calcining conditions and as such experiences an essentially instantaneous thermal shock. The actual temperature to be employed during calcination is influenced by several considerations. For example, it appears that too low of a calcination temperature will not be sufficiently energetic to drive the phase transition from the precursor to vanadium pyrophosphate. In addition, too high or too low of a temperature relative to 390° C. leads to a higher rate of oxidation of the catalyst and tends to give catalyst with too high an oxidation state (i.e., too high of an average $V_{ox}$). A 300 gram catalyst precursor sample calcined in a fluid bed reactor at 360° C. and 35 psig air containing 3 mole percent steam exhibited a higher rate of catalyst oxidation and lower maleic yield during use relative to similar experimental runs at 390° C. Similarly higher catalyst oxidation rates and lower maleic yields were obtained with catalyst calcination temperatures of 370° C. and 420° C. versus 390° C. These differences are also evident in the x-ray diffraction patterns of the respective samples. The precursor sample calcined at 360° C. is oxidized as it is transformed through an amorphous intermediate directly to a semi-amorphous VOPO$_4$ phase. In contrast, the precursor calcined at temperatures higher than 390° C. transform first to the desired pyrophosphate phase, but quickly convert to more highly oxidized VOPO$_4$ phase. The data indicating that a higher temperature is necessary for proper calcination are consistent with the thermal gravimetric analysis (TGA) measurements in that a significant event near 370° C. is observed. Thus a temperature of at least 370° C. is necessary to achieve the desired phase transition. This lower limit for calcination is also felt to be influential in terms of the desired oxidative removal of entrained hydrocarbons typically present in the V/P/O catalyst precursor. In other words, calcination performed at 370° C. and above produces the desired phase transition to the pyrophosphate phase thus leading to effective oxidation rates and removal of entrained organics. The lower practical temperature limit for the phase transition when performed in a commercial scale recirculating bed reactor appears to be more near 380° C. for calcination at 3.5 atm. Preferably a calcination temperature of 390±5° C. should be used.

The upper limit to the calcination temperature is also influenced by several considerations. For example, higher calcination temperatures tend to favor higher average $V_{ox}$, and a $V_{ox}$ of 4.6 or greater categorically leads to inferior catalyst performance. Thus, the previous experimental run at 420° C. and 35 psig produced calcined catalyst capable of improved maleic yield provided the $V_{ox}$ was maintained during calcination at a value of 4.55 or below. But a similar experimental run at 460° C. did not result in improved V/P/O catalyst demonstrating that calcination temperature appears to affect maleic yield independent of oxidation state. Again the preferred calcination temperature appeared to be 390° C., as higher and lower temperatures both increased the rate of formation of over-oxidized catalyst and reduced the maleic yield when tested in a fixed bed and riser reactor.

Rapid temperature rise of the catalyst precursor in an oxygen containing gas insures quick combustion and removal of entrained organics in the catalyst precursor. Simultaneously the rapid temperature rise associated with the introduction of catalyst precursor into an already hot fluidized gaseous stream leads to quick loss of water of hydration and hence calcination of the catalyst. It is presently felt that the combination of quick removal of entrained organics and typically about 10 weight percent loss of water may contribute beneficially to an observed increase in resulting catalyst surface area (typically as high as 30 to 35 m$^2$/g). This relative increase in surface area may also contribute to the observed increase in ultimate catalyst activity (typically as much as 20 to 25% or greater). This quick temperature rise and rapid removal of entrained organics and water of hydration created by immersing the catalyst precursor into an already hot fluidized bed under oxidative conditions at a controlled rate of addition that sustains the high temperature is also felt to be critical in distinguishing the improved method of calcining and activating V/P/O catalyst according to the instant invention from the prior art techniques. In perhaps the broadest yet most simplistic sense the improved method of the present invention can be viewed as a method of calcining V/P/O catalyst precursor by subjecting the precursor to a temperature of 390±5° C. in a fluidized state for sufficient time to remove entrained organics and water of hydration such as to produce and average $V_{ox}$ greater than 4.05 but less than 4.55. Such a calcined V/P/O catalyst precursor can then be stored for sustained periods of time in an essentially non-oxidizing environment (i.e., typically a dry gaseous phase having an oxygen partial pressure of less than 0.035 atm) at essentially any temperature and then produce upon activation, including mere in-situ use at operating conditions, a V/P/O catalyst that consistently exhibits significantly increased catalyst activity relative to vapor phase oxidation of n-butane to maleic anhydride whether the reaction is performed in a fixed bed, fluidized bed or transfer fluidized bed reactor.

Pressure

The calcination pressure significantly influences both the maleic yield and the oxidation rate of the resulting V/P/O catalyst. Several calcination experiments were carried out with pressures of 1, 3.5, and 6 atm. respectively. All experiments were conducted at 390° C. using air feed gas containing 3 mole percent water vapor. The catalyst performance was evaluated in an automated fixed bed reactor after calcination of the V/P/O catalyst precursor in a pressurized fluid bed reactor. The automated fixed bed reactor evaluations of the resulting catalyst indicate that although the 1 atm and 3.5 atm calcinations activate differently, both produce ultimately catalyst of markedly improved activity. However the high pressure (6 atm) catalysts are poor. Typically the catalyst calcined at the respective three pressures to a final $V_{ox}$ approaching 4.55 when evaluated in the automated fixed bed reactor will show inferior maleic yield as a function of time for high pressure (i.e., 6 atm of air) catalyst and sustained superior maleic yield as a function of run time for 3.5 atm calcined catalyst. The 1 atm catalyst will typically exhibit an improved initial maleic yield which increases for the first 50 to 100 hours of operation ultimately surpassing the performance of the 3.5 atm catalyst. It should be appreciated that this pressure influence for purposes of claiming the present invention should perhaps be more accurately viewed as being a partial pressure of oxygen effect rather than a total pressure effect. As such, the reference to the total pressure limitation will utilize the expression "atm of air" when referencing an upper operating limitation.

Calcination pressure also has a significant effect on the oxidation state of the vanadium in the calcining V/P/O catalyst. The average vanadium oxidation state as a function of time for calcinations at 1, 3.5, and 6 atm and 390° C. using air with 3 mole percent water vapor shows that the oxidation rate of the precursor increases with increasing pressure. Thus, lower calcination pressures could be used to extend the acceptable calcination time relative to higher pressure. Since this is felt to be an oxygen partial pressure effect an extension of the acceptable calcination time can be achieved by diluting the air with an inert gas or in fact the time could be shortened by enriching the oxygen content. Similarly, performing the calcination in a fluidized state in a batch mode will afford a different residence time before over oxidation of the precursor relative to the alternative of calcining in the regenerator. The continuous or semi-continuous mode associated with calcination in the regenerator of a recirculating solids reactor and the inherent back-mixing taking place in the periodical transfer of calcined catalyst to the riser section requires shorter average residence times to ensure a high percentage of calcined catalyst is not over oxidized. Typically at 390° C. using air with 3 mole percent water at 3.5 atm in a batch mode operated fluidized reactor, a calcination residence time for achieving a $V_{ox}$ of 4.6 would require 35 to 40 hours. In contrast, the back-mixing mode associated with the commercial scale start-up procedure in the recirculating solid reactor plant involves typically a 4 hour or less residence time at 390° C. using air with 3 mole percent water at 3.5 atm and higher pressure, and up to about 20 hours residence time at 1 atm of air. Again, the residence time in the back-mixing mode can be controlled an/or influenced by diluting or enriching the oxygen content of the air thus producing greater flexibility in selecting the corresponding residence time and operating pressure.

The partial pressure of water vapor in the oxygen containing gas phase used to calcine the catalyst precursor can also play a role and influence the $V_{ox}$ as well as the rate of oxidation during calcination. Preferably the calcination should be performed with a dry gas. A completely dry gas during calcination tends to inhibit over oxidation of the catalyst precursor resulting in a $V_{ox}$ approaching 4.5. In contrast the presence of water vapor during calcination tends to promote over oxidation as the time of calcining in a wet oxidative environment is extended beyond the previous mentioned limits. As a pragmatic design consideration, particularly relative to large scale commercial plants, the concept of using direct fire heating of air employing a hydrocarbon fuel such as n-butane or the like will inherently result in steam/water vapor being present during calcination. Similarly, any entrained organics when subjected to oxidative calcination gas will represent a source of water. However as illustrated and explained above, water vapor concentrations typical of direct fire heating of the gas phase can be tolerated in the processes of the instant invention.

The V/P/O precursor compositions, which are converted to active catalyst by the process of this invention can be made using the procedures as generally known and practiced in the art. Preferably the V/P/O precursor can be made using the procedures described in U.S. Pat. No. 4,371,702, the teaching of which is incorporated by reference herein. The process of this invention is also applicable to the attrition resistant V/P/O-SiO$_2$ precursor composition described in U.S. Pat. No. 4,677,084, the teaching of which is incorporated by reference herein.

The following example is presented to more fully demonstrate and further illustrate various individual aspects and features of the present invention and verify advantages of the present invention. As such the example is felt to be non-limiting and is meant to illustrate the invention but is not meant to be unduly limiting in any way particularly with respect to ultimate properties of the improved catalyst and utility of the claimed improved process.

EXAMPLE

A commercial scale fluidized transfer bed plant for direct oxidation of n-butane to maleic anhydride involving a riser reactor for n-butane oxidation and a separate fluidized bed reactor for regeneration of catalyst was started up by continuously adding spray dried V/P/O catalyst precursor at a nominal rate of about 10 thousand pounds per hour to the regeneration zone. During catalyst addition the calcining fluidized bed of catalyst precursor within the regeneration reactor was maintained at 390° C. and 2.7 atm by use of hot air which contained approximately 19% oxygen after direct fire heating using n-butane as fuel. The calcining catalyst precursor was periodically removed from the regenerator reactor and transferred to the riser reactor of the plant at a rate such as to have an average residence time in the regenerator under oxidative calcination conditions of from 3.25 to 3.5 hours. The calcined catalyst precursor transferred to the riser reactor was maintained at an operating temperature not more than 50° C. less than the calcination temperature by use of recirculating nitrogen until the entire charge of catalyst had been added and calcined. Upon commencement of circulating the fluidized catalyst charge and introduction of n-butane to the riser reactor, the catalyst quickly reached a maleic production rate 25% greater than that previously experienced for such V/P/O catalyst.

The benefits and advantages of the of the methods according to the present inventions are felt to be significant and numerous. First and foremost, the improved method of starting-up a recirculating solids reactor when applied on a commercial scale represents a simplified and streamlined in situ calcination procedure wherein spray dried catalyst precursor is continuously added to the regenerator at a rate that allows for maintaining the temperature of the fluidized bed and simultaneously affords the periodical discharging of equivalent quantities of calcined catalyst from the regenerator to the riser side of the reactor. Consequently, the start-up procedure affords control and optimization of the temperature rise, combustion of the entrained organics and average residence time of the catalyst precursor the combination of which ultimately leads to activated catalyst of improved activity and surface area without significant loss in selectivity. For large scale commercial recirculating bed reactor type plants this leads to a sizable reduction in start-up time measured in terms of weeks and a relaxation of the need to control the average $V_{ox}$ during calcination within a narrow range about the value 4.0. For all types of applications this leads to V/P/O catalysts of up to 25% higher activity or even greater.

Having thus described and exemplified the invention with a certain degree of particularity, it should be appreciated that the following claims are not to be so limited but are to be afforded a scope commensurate with the wording of each element of the claim and equivalents thereof.

We claim:

1. In a process for selective vapor phase oxidation of n-butane to maleic anhydride involving the use of a recirculating solids reactor comprising a reaction zone and a catalyst regeneration zone wherein n-butane is converted to maleic anhydride in the reaction zone of the recirculating solids reactor by use of a vanadium/phosphorous oxide (V/P/O) catalyst in oxidized form and the reduced vanadium/phosphorous oxide catalyst is regenerated by contact with oxygen in the regeneration zone of the recirculating solids reactor; the specific improvement comprising: (i) adding catalyst precursor to the regeneration zone maintained at a temperature between 380° C. and 400° C.; (ii) maintaining said catalyst precursor in a fluidized state within the regeneration zone by use of air or oxygen containing gas for a sufficient time and pressure to remove entrained organics and to at least partially dehydrate said catalyst precursor; (iii) transferring calcined catalyst precursor from the regeneration zone to the reaction zone such as to maintain an average residence time for catalyst precursor in the regeneration zone resulting in an average $V_{ox}$ of 4.55 or less; and (iv) maintaining said calcined catalyst precursor in a fluidized state within the reaction zone near operating temperature using a substantially non-oxidizing gas until catalyst circulation is commenced.

2. A process of claim 1 wherein said rate of addition of catalyst precursor is coordinated simultaneously with said transferring of calcined catalyst precursor from the regeneration zone to the reaction zone such as to maintain the temperature within the regeneration zone until the entire charge of catalyst is calcined.

3. A process of claim 1 wherein charge of calcined catalyst precursor is activated, in situ, under operating conditions with introduction of n-butane to the reaction zone and catalyst recirculation between the reaction zone and the regeneration zone.

4. A process of claim 1 wherein said catalyst precursor in a fluidized state within the regeneration zone is maintained at a temperature of 390±5° C. at a pressure of up to about 3.5 atm and said average residence time for catalyst precursor in the regeneration zone is maintained at about 4 hours or less.

5. A process of claim 1 wherein said average range of residence time for catalyst precursor in the regeneration zone is less than about 4 hours at 3.5 atm of air or above and up to 20 hours at 1 atm of air.

6. A process of claim 1 wherein said temperature range of 380° C. to 400° C. is achieved by direct fire heating using n-butane resulting in a water vapor content in said air or oxygen containing gas of up to about 3 mole %.

7. A process for calcining V/P/o catalyst comprising the steps of:
   (a) establishing a gas flow within a fluidized bed reactor using air or oxygen containing gas at a temperature range of 370° C. to 420° C.;
   (b) adding to the fluidized bed reactor of step (a) a hydrated V/P/O or V/P/O-SiO$_2$ catalyst precursor at a rate such that said catalyst precursor experiences a rapid temperature rise in a fluidized bed state to a temperature range of 370° C. to 420° C.;
   (c) maintaining said catalyst precursor of step (b) in a fluidized state at said temperature range for a sufficient time and pressure to remove entrained organics and to dehydrate said catalyst precursor while simultaneously achieving an average $V_{ox}$ in excess of 4.05 but not in excess of 4.55; and
   (d) recovering and storing the calcined V/P/O catalyst produced in step (c) in a non-oxidizing gas.

8. A process of claim 7 wherein said catalyst precursor is added to a fluidized bed maintained at a temperature of 390±5° C.

* * * * *